(12) United States Patent
Meyer et al.

(10) Patent No.: US 12,307,007 B2
(45) Date of Patent: May 20, 2025

(54) METHOD FOR A PUPIL DETECTION AND/OR PUPIL TRACKING, OPTICAL SYSTEM AND SMART GLASSES

(71) Applicant: Robert Bosch GmbH, Stuttgart (DE)

(72) Inventors: Johannes Meyer, Magstadt (DE); Johannes Fischer, Pliezhausen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 291 days.

(21) Appl. No.: 18/174,836

(22) Filed: Feb. 27, 2023

(65) Prior Publication Data

US 2023/0288986 A1 Sep. 14, 2023

(30) Foreign Application Priority Data

Mar. 4, 2022 (DE) ............ 10 2022 202 208.4

(51) Int. Cl.
*G06F 3/01* (2006.01)
*A61B 3/103* (2006.01)
*G02B 5/32* (2006.01)
*G02B 27/00* (2006.01)
*G02B 27/01* (2006.01)

(52) U.S. Cl.
CPC ......... *G06F 3/013* (2013.01); *G02B 27/0093* (2013.01); *G02B 27/017* (2013.01); *A61B 3/103* (2013.01); *G02B 5/32* (2013.01); *G02B 2027/0178* (2013.01)

(58) Field of Classification Search
CPC ............ A61B 3/103; G02B 2027/0178; G02B 27/0093; G02B 27/017; G02B 5/32; G06F 3/013
See application file for complete search history.

(56) References Cited

U.S. PATENT DOCUMENTS

| 11,307,654 B1 * | 4/2022 | Zhang | G06V 10/94 |
| 2021/0223549 A1 * | 7/2021 | Maimone | G02B 17/004 |
| 2023/0194882 A1 * | 6/2023 | Yu | G02B 27/0093 |
| | | | 359/13 |

FOREIGN PATENT DOCUMENTS

| WO | WO-0248760 A1 * | 6/2002 | ........... G02B 5/0221 |
| WO | WO-2022263255 A1 * | 12/2022 | ......... G02B 27/0093 |

* cited by examiner

*Primary Examiner* — Mark R Gaworecki
(74) *Attorney, Agent, or Firm* — NORTON ROSE FULBRIGHT US LLP

(57) ABSTRACT

A method for a pupil detection and/or pupil tracking with the aid of an evaluation of a speckle pattern back-reflected by an eye of a light of an infrared laser irradiated into the eye. At least the light of the infrared laser irradiated into the eye is scanned via a holographic optical element that includes different refractive structures, the different refractive structures being configured in such a way that they each generate a different visual defect correction.

11 Claims, 3 Drawing Sheets

METHOD FOR A PUPIL DETECTION AND/OR PUPIL TRACKING, OPTICAL SYSTEM AND SMART GLASSES

CROSS REFERENCE

The present application claims the benefit under 35 U.S.C. § 119 of German Patent Application No. DE 10 2022 202 208.4 filed on Mar. 4, 2022, which is expressly incorporated herein by reference in its entirety.

BACKGROUND INFORMATION

A method for a pupil detection and/or pupil tracking with the aid of an evaluation of a speckle pattern back-reflected by the eye of a light of an infrared laser radiated into the eye has already been provided in the related art.

SUMMARY

The present invention is directed to a method, in particular, for smart glasses, for a pupil detection and/or pupil tracking with the aid of an evaluation of a speckle pattern back-reflected by an eye, in particular, by a retina of the eye, of a light of an infrared laser radiated into the eye.

According to an example embodiment of the present invention, it is provided that at least the light of the infrared laser radiated into the eye is scanned via a holographic optical element (HOE), which includes different refractive structures, the different refractive structures being designed in such a way that they each generate a different visual defect correction, preferably, in each case a visual defect correction of different degrees. In this way, it is possible to advantageously achieve a reliable pupil detection and/or pupil tracking, in particular, also in persons that have visual defects (for example, myopia or hyperopia), preferably also with the aid of the method of evaluating back-reflected speckle patterns. The HOE includes, in particular, at least two, preferably more than two, for example, three, four, five, six or more than six different refractive structures for different visual defects, in particular, for different degrees of visual defect. An optical function differing from the further refractive structures is, in particular, written into each of the different refractive structures. For example, a refractive structure adapted to a particular diopter number is written into each of the different refractive structures, for example, there could be five different refractive structures, each one being adapted to one of the following degrees of visual defect: −2 diopter, −1 diopter, 0 diopter, +1 diopter, and +2 diopter. The different refractive structures are, in particular, all integrated into a single (interconnected) HOE. The HOE is, in particular, designed to be written with a number of different optical elements/optical functions. The infrared laser is, in particular, scanned via multiple of the different refractive structures of the HOE, preferably via all of the different refractive structures of the HOE, as a result of which a number of images separated from one another corresponding to the number of different refractive structures, focal planes and/or focal points, in particular, in the area of the eye is generated. The refractive structures intended to generate "visual defect corrections" is understood to mean, in particular, that the refractive structures manipulate the beam path of the radiated light in such a way that an incidence of the beam path onto the retina, in particular, a focusing of the beam path onto the retina is achieved by the manipulation, as would be the case in a healthy (non-visually defective) eye. A speckle pattern (also: laser granulation) is, in particular, an interference phenomenon grainy in appearance, which may be observed with sufficiently coherent lighting of optically coarse object surfaces such as, for example, the retina of the eye. The light used for the evaluation is, in particular, detected by an infrared detector, which is designed/situated on-axis with the infrared laser. The light/speckle patterns back-reflected in the laser direction, in particular, are measured and used for the evaluation. For example, the back-reflected light/speckle pattern is detected by a photodiode in a back-reflector of the infrared laser (for example, ViP=VCSEL with integrated photodiode), in particular, as in the case of an LFI sensor (Laser Feedback Interferometry Sensor). Alternatively, a photodiode could be folded into the infrared laser beam via a beam splitter and/or combiner. "Smart glasses" are understood, in particular, to mean a wearable (head-mounted) display, with the aid of which pieces of information about the field of vision of a user may be added. Smart glasses preferably allow for augmented reality and/or mixed reality applications. Data glasses are generally also referred to as smart glasses.

According to an example embodiment of the present invention, it is further provided that the different refractive structures are designed in such a way that for the light of the infrared laser radiated into the eye, different focal points are generated in each case in the eye, in particular, at different distances to an eye lens of the eye, in particular, in cooperation with the respective eye lens. In this way, a reliable pupil detection and/or pupil tracking may be advantageously achieved, in particular, also in the case of persons with visual defects (for example, myopia or hyperopia). The different refractive structures included in the HOE/the different optical elements included in the HOE, in particular, focus in each case the radiated collimated light of the infrared laser onto the retina of the eye. The individual refractive structures included in the HOE/the individual optical elements included in the HOE, in particular, generate in each case an individual focal plane. These focal planes generated by the refractive structures/optical elements are, in particular, situated at different distances to the HOE and/or to the eye lens of the irradiated eye. In particular, a strong backscattering by the retina of the light radiated into the eye, in particular, a backscattering by the retina of the radiated light into the eye sufficient for the evaluation of the speckle pattern back-reflected by the eye, takes place only when the light of the infrared laser radiated into the eye is focused on the retina, in particular, in cooperation with the eye lens. If the eye is now visually defective (a refractive power of the lens differs from the refractive power of a healthy lens/the retina is situated outside the focal point of the lens), the result is that a light beam generated for a healthy eye (0 diopter) is focused in front of or behind the retina and thus no sufficient reflection signal is generated. A focusing is therefore generated, in particular, by at least one of the refractive structures, preferably by a plurality of the refractive structures, whose focal position, compared, in particular to the refractive structure for the healthy eye, is shifted forward or backward in the eye (for example, by 1 mm).

According to an example embodiment of the present invention, it is also provided that a visual defect of the eye is ascertained with the aid of an analysis of a beam path of the speckle pattern back-reflected by the eye, in particular by a mapping of the beam path of the speckle pattern back-reflected by the eye.

In this way, a particular simple recognition of visual defects and/or adaptation to different visual defects may be advantageously achieved. The visual defect is ascertained, in particular, free of and/or regardless of mobile optical elements, such as focal lenses (cf. medical refractometer). In the analysis/in the mapping of the beam path, it is ascertained, in particular, from which of the different refractive structures the back-reflected speckle pattern originates. In particular, only the light that was focused onto the retina of the eye and, in particular, where it has generated a speckle pattern, is sufficiently back-reflected. Since each of the different refractive structures is assigned a diopter number, it is then possible to determine from the latter the visual defect. Each of the different refractive structures of the HOE, in particular, generates a reflection beam extending differently in space, so that the respective individual refractive structure of the HOE may be deduced via an ascertainment of the position of the detected reflection beam (mapping).

According to an example embodiment of the present invention, it is further provided that a development of a visual defect of the eye is ascertained with the aid of an analysis of a temporal change of a beam path of the speckle pattern back-reflected by the eye. As a result, it is advantageously possible to recognize in a timely and/or particularly simple manner a development of a visual defect, for example, of an age-related visual defect. As a result, a high degree of user comfort of smart glasses may be advantageously achieved, in particular, since in the display of the smart glasses it is possible to counteract an emerging visual defect in a timely manner. To recognize the development of a visual defect of the eye, an analytical result/a mapping result for identified eyes is, in particular, stored periodically, for example, daily, weekly, monthly, or annually and compared with previous analytical results/mapping results of the same eye.

Furthermore, according to an example embodiment of the present invention, an optical system is provided for carrying out the above-described method using a laser projector at least to generate a scanned infrared laser beam and using a holographic-optical element (HOE) that includes different refractive structures. A reliable pupil detection and/or pupil tracking, in particular, in persons with visual defects (for example, myopia or hyperopia), preferably also with the aid of the method of evaluating back-reflected speckle patterns may be thereby advantageously achieved. The laser projector also includes, in particular, the infrared detector. The laser projector includes, in particular, a ViP. The laser projector forms, in particular, one projection component of a virtual retinal display (retinal scan display). The laser projector is also designed, in particular, to generate a scanned laser beam reproducing a visible image. "Provided" is understood to mean, in particular, specifically programmed, designed and/or fitted. An object being provided for a particular function is understood to mean, in particular, that the object fulfills and/or carries out this particular function in at least one application state and/or operating state. The different refractive structures are, in particular, combined in one single HOE. The HOE is integrated, in particular, into a lens of the smart glasses.

According to an example embodiment of the present invention, it is further provided that the HOE has a segmented design, at least two different segments of the HOE including different refractive structures for different visual defect corrections. This may advantageously enable a particularly simple visual defect determination, for example, by a mapping. The scanned infrared laser beam is scanned, in particular, via both, preferably via all, segments of the HOE. The segmented HOE includes, in particular, more than two, for example, three, four, five, six or more than six segments, each including different refractive structures for different visual defects and/or for different degrees of visual defect, in particular, respectively different visual defect corrections. Another optical function, in particular, another focusing reflection hologram is, in particular, written into each segment. Different visual defect corrections may be provided for correcting different visual defects (myopia/hyperopia) and/or for correction of different degrees of visual defect (different diopter numbers). The segments of the segmented HOE are situated, in particular, in a shared plane.

According to an example embodiment of the present invention, a compact design may be advantageously facilitated if the different refractive structures, in particular, the segments, in which the HOE are situated in a linear manner or in a, in particular, regularly repeating pattern made up of rhombuses, triangles or other shapes. A reliable visual defect determination, in particular, with the aid of a precise mapping, may advantageously also be achieved. The different refractive structures, preferably, the segments, may, in particular, be arranged in a checkerboard pattern, where individual or all pattern fields could also have shapes differing from squares. As an alternative to a discrete delimitation of the refractive structures, in particular, of the segments, a transition between refractive structures could also be provided. For example, a sine function could be utilized, which causes a continuous change of the refraction between two segments.

According to an example embodiment of the present invention, a particularly precise visual defect determination may be advantageously facilitated if, in addition, lines or pattern fields of the HOE that include the different refractive structures, in particular, that form the segments, have a sufficiently large spatial extension, which allows for a mapping of a back-reflected speckle pattern for ascertaining the respectively optimal refractive structure. The segments in this case have, in particular, a minimum extension in a direction at least essentially in parallel to a scan direction of the scanned infrared laser beam of at least 10 µm, preferably of at least 30 µm, preferably of at least 60 µm and particularly preferably of at least 100 µm. "Essentially in parallel" is understood here to mean, in particular, an orientation of a direction relative to a reference direction, in particular, in a plane, the direction exhibiting a difference compared to the reference direction of, in particular, less than 8°, advantageously less than 5° and particularly advantageously less than 2°. The respective refractive structure referred to as "optimal" is designed, in particular, as the refractive structure of the plurality of refractive structures of the HOE, in particular, as the reflection hologram of the plurality of reflection holograms of the HOE, which best focuses the radiated light of the infrared laser, and optionally also of a visible light, onto the retina of the eye of the respective user, in particular, which generates a focal point of the radiated light of the infrared laser, and optionally also of the visible light, which is situated closest to the retina of the eye of the respective user. The pattern fields may form a Bayer pattern.

According to an example embodiment of the present invention, a high spatial resolution of the pupil detection may be advantageously achieved if, alternatively, the lines or pattern fields of the HOE including the different refractive structures have a spatial extension, which is smaller than the one necessary for a mapping of a back-reflected speckle pattern. This may advantageously enable a particularly accurate recognition of a pupil shape, of a pupil size and/or of a pupil size. The segments in this case have, in particular, a minimum extension in an at least essentially parallel direction to a scan direction of the scanned infrared laser beam of not more than 20 µm, preferably not more than 10 µm, preferably not more than 5 µm and particularly preferably not more than 3 µm.

According to an example embodiment of the present invention, it is further provided that the optical system includes an infrared detector for detecting a reflection of the infrared light beam, in particular, directly and/or diametrically reflected opposite a laser emitting direction of the infrared laser beam, in particular by a retina of the eye. A high precision of the visual defect recognition and/or of the visual defect correction may be advantageously achieved as a result. The infrared detector is integrated, in particular, into the laser projector/into a light source for generating the infrared beam, for example, as a ViP.

Furthermore, according to an example embodiment of the present invention, smart glasses are provided for carrying out the above-described method and/or for including the optical system. A reliable pupil detection and/or pupil tracking, in particular, in persons with visual defects (for example, myopia or hyperopia), preferably also with the aid of the method of evaluation of back-reflected speckle patterns, may be advantageously achieved as a result.

The method according to the present invention, the optical system according to the present invention, and the smart glasses according to the present invention are not to be limited here to the above-described application and specific embodiment. The method according to the present invention, the optical system according to the present invention, and the smart glasses according to the present invention may, in particular, include a number of individual elements, components and units as well as method steps that differ from a number cited herein for fulfilling a functionality described herein. In addition, in the case of the value ranges specified in this description, values lying also within the cited limits are to be considered described and arbitrarily usable.

BRIEF DESCRIPTION OF THE DRAWINGS

Further advantages result from the following description. An exemplary embodiment of the present invention is represented in the figures. The figures, and the description contain numerous features in combination. Those skilled in the art will also purposely consider the features individually and combine them to form meaningful further combinations.

DETAILED DESCRIPTION OF EXAMPLE EMBODIMENTS

Figure 1:
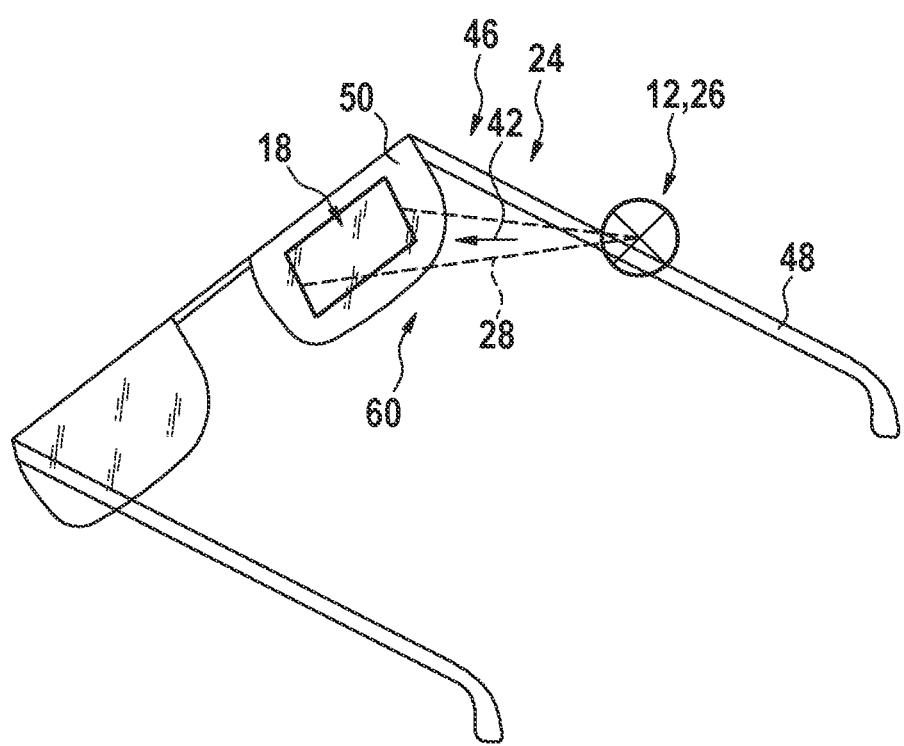
FIG. 1 schematically shows a representation of smart glasses including an optical system, according to an example embodiment of the present invention.

FIG. 1 schematically shows a representation of smart glasses 46. Smart glasses 46 include an eyeglass frame 48. Smart glasses 46 include eyeglass lenses 50. Smart glasses 46 form an eye accommodation area 60 situated behind eyeglass lenses 50 and between frame temples of eyeglass frame 48. Smart glasses 46 include an optical system 24. Optical system 24 is provided for forming a virtual retina display. Optical system 24 is provided for projecting images directly onto a retina 44 of an eye 10 (cf. FIG. 3). Optical system 24 includes a laser projector 26. Laser projector 26 is integrated at least partially into eyeglass frame 48. Laser projector 26 is provided for generating a visible scanned laser beam (not represented), which is provided for the purpose of projecting the image onto retina 44 of eye 10 of a wearer of smart glasses 46. Laser projector 26 includes a MEMS laser projection system for generating and outputting the images. Laser projector 26 includes an infrared laser 12. Laser projector 26, in particular, infrared laser 12, is provided for generating a scanned infrared beam 28. Infrared laser beam 28 is provided for use in a method for a pupil detection and/or pupil tracking. Infrared laser beam 28 is provided for generating a speckle pattern on retina 44 of eye 10. The method for pupil detection and/or pupil tracking is based in this case on an evaluation of a reflection of infrared laser beam 28 back-reflected by retina 44 of eye 10. Optical system 24 includes an infrared detector 40. Infrared detector 40 is provided for detecting the reflection of infrared laser beam 28 back-reflected by retina 44 of eye 10. Infrared detector 40 is situated in such a way that a detection of a reflection of infrared laser beam 28 back-reflected opposite a laser emitting direction 42 of infrared laser beam 28 is facilitated by infrared detector 40. Infrared detector 40 is formed by laser projector 26. Infrared detector 40 is integrated into laser projector 26. At least one of eyeglass lenses 50 forms an optical element of optical system 24. Optical system 24 includes a holographic optical element (HOE 18). HOE 18 is integrated into eyeglass lens 50. HOE 18 is provided for reflecting irradiated light.

Figure 2A:
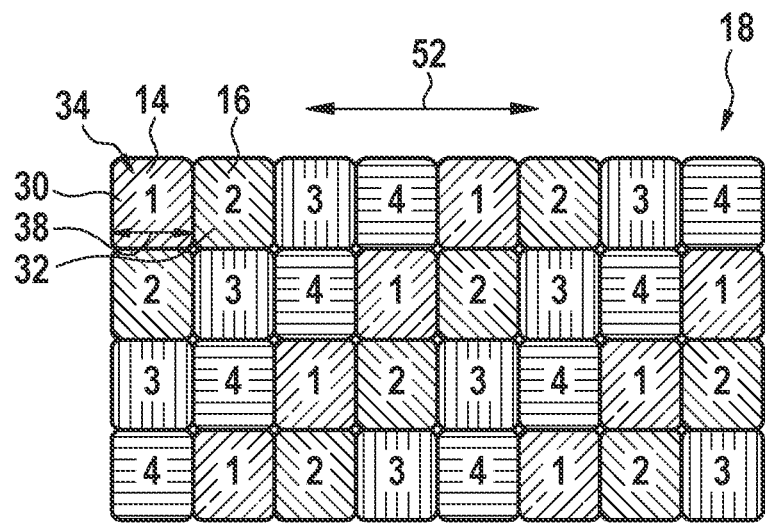
FIG. 2A schematically shows a first possible design of a holographic-optical element of the optical system, according to an example embodiment of the present invention.
Figure 2B:
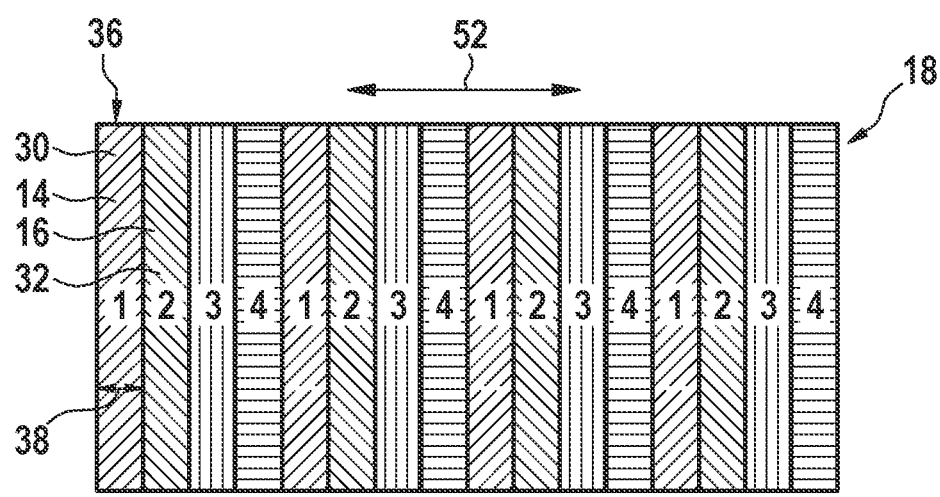
FIG. 2B schematically shows a second possible design of the holographic-optical element of the optical system, according to an example embodiment of the present invention.

FIGS. 2A and 2B schematically show two possible structures of HOE 18. HOE 18 has a segmented design. HOE 18 includes multiple segments 30, 32. HOE 18 includes different refractive structures 14, 16. Each segment 30, 32 forms one of the different refractive structures 14, 16. The different refractive structures 14, 16 are provided for generating different visual defect corrections. The different refractive structures 14, 16 are provided for generating different degrees of visual defect corrections. The different refractive structures 14, 16 are designed in such a way that they each generate a different visual defect correction and/or a different degree of a visual defect correction. The different refractive structures 14, 16 are designed to focus differently. The different refractive structures 14, 16 are designed in such a way that they generate different focal points 20, 22 each in the eye 10 for the light of infrared laser 12 (cf. FIG. 3b).

In the exemplary embodiment of HOE 18 from FIG. 2A, the different refractive structures 14, 16 are situated in a regularly repeating pattern made up of quadratic rhombuses. The pattern in this case includes pattern fields 34. In the exemplary embodiment of HOE 18 from FIG. 2B, the different refractive structures 14, 16 are situated in lines 36 in a linear manner next to one another. In both FIGS. 2A and 2B, a scan direction 52 of scanned infrared laser beam 28 is indicated by an arrow. Scan direction 52 is the direction in which infrared laser beam 28 is moved rapidly back and forth during an image generation. During a rapid back and forth scanning of scanned infrared laser beam 28 along scan direction 52, infrared laser beam 28 is also moved slowly upward and downward. Lines 36 or pattern fields 34 of HOE 18 that include the different refractive structures 14, 16 each have a spatial extension 38 in scan direction 52. Spatial extension 38 of pattern fields 34 or of lines 36 is large enough to allow a mapping of the speckle pattern back-reflected by retina 44 of eye 10 for ascertaining respectively optimal refractive structure 14, 16 for an optimal visual defect correction. Alternatively, spatial extension 38 of pattern fields 34 or lines 36 may also be smaller than that required for a mapping of a back-reflected speckle pattern (not represented).

Figure 3:
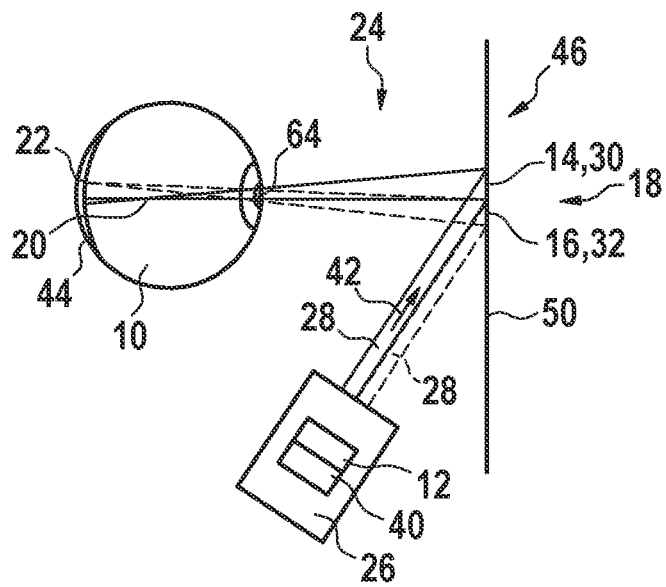
FIG. 3 shows an exemplary beam path of an infrared laser beam of the optical system, according to an example embodiment of the present invention.

FIG. 3 shows by way of example beam paths of infrared laser beam 28 for an eye 10. Refractive structures 14, 16 each generate focal points 20, 22 in eye 10. A first refractive structure 14 of refractive structures 14, 16 generates in this case a focal point 20, which is situated in front of retina 44. A second refractive structure 16 of refractive structures 14, 16 generates a focal point 22, which is situated on retina 44. For this example, it is assumed that in this case eye 10 is myopic. First refractive structure 14 in this example is correction-free, i.e., is provided for generating a focusing which, in the case of a healthy (0 diopter) eye, would land on retina 44. In myopic eye 10, focal point 20 generated by first refractive structure 14 is situated in front of retina 44. In a hyperopic eye, focal point 20 of the same refractive structure 14 would be situated behind retina 44. Second refractive structure 16 in this example is designed to be myopia-correcting, i.e., is provided for the purpose of generating a focusing which, in the case of a healthy (0 diopter) eye, would land away from retina 44. In myopic eye 10, focal point 22 generated by second refractive structure 16 is situated on retina 44. In the case of a hyperopic eye, focal point 22 of the same refractive structure 16 would be situated even further behind retina 44. Further refractive structures not represented may then be provided to generate stronger or weaker myopia corrections than second refractive structure 16 or to generate hyperopia corrections of different degrees. A backtracking of the beam paths represented in FIG. 3 is called mapping and allows an identification of refractive structure 14, 16, which places focal point 20, 22 in respective eye 10 onto retina 44.

Figure 4:
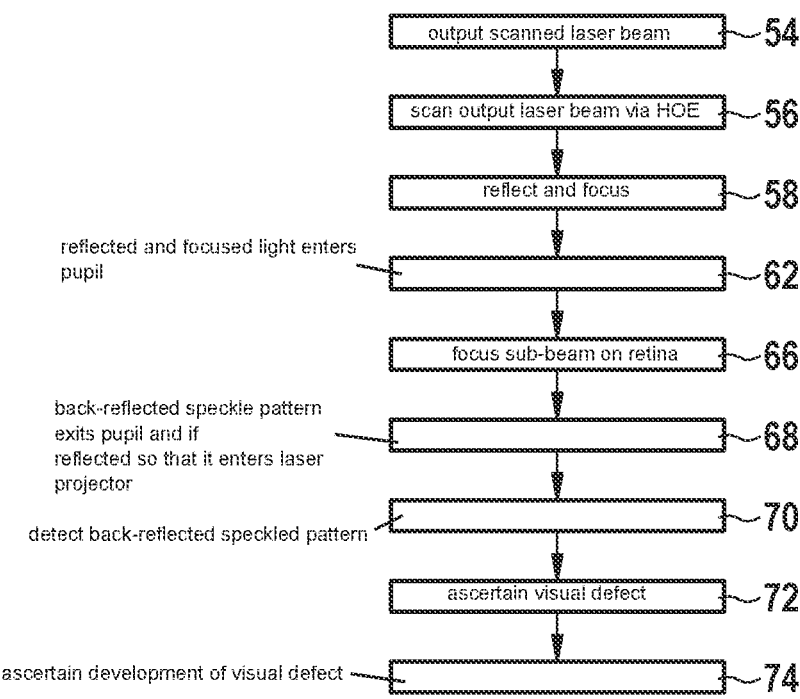
FIG. 4 schematically shows a flowchart of a method for a pupil detection and/or pupil tracking, according to an example embodiment of the present invention.

FIG. 4 schematically shows a flowchart of a method for a pupil detection and/or pupil tracking. The method is based on an evaluation of a speckle pattern back-reflected by an eye 10 of a light of an infrared laser 12 irradiated into eye 10. In at least one method step 54, a scanned laser beam that includes at least infrared laser beam 28 is output by laser projector 26.

The scanning of the laser beam takes place in this case via a deflection of the laser beam with the aid of a MEMS mirror array (not represented). In at least one further method step 56, at least output infrared laser beam 28 is scanned via HOE 18 that includes the different refractive structures 14, 16. In the process, infrared laser beam 28 sweeps over a plurality of segments 30, 32 of HOE 18, each of which may include different refractive structures 14, 16. The different refractive structures 14, 16 are designed in such a way that they each generate a different visual defect correction. In at least one further method step 58, refractive structures 14, 16, designed, in particular, as reflection holograms, reflect and focus the light of infrared laser beam 28 incident upon them in the direction of eye accommodation area 60 of smart glasses 46, in particular in the direction of eye 10 of the user of smart glasses 46. In at least one further method step 62, the light of infrared laser beam 28 reflected and focused by refractive structures 14, 16 enters through a pupil 64 of eye 10 into an interior of eye 10. In the process, the light of infrared laser beam 28 passes an eye lens (not represented) of eye 10. The light of infrared laser beam 28 entering into eye 10 as a function of the refractive power of the eye lens is further bent/focused. As a result of the respective different design of the different refractive structures 14, 16 and the resulting differences of the sub-beams of the light of infrared laser 12 irradiated into eye 10 originating from respective refractive structures 14, 16 and entering into pupil 64, respectively different focal points 20, 22 are generated in the process in eye 10 for the respective sub-beams. In at least one further method step 66, one of the sub-beams is focused on retina 44 of eye 10 or very close to retina 44 of eye 10. This sub-beam focused on retina 44 produces, triggered by the uneven surface of retina 44 (rods/little pins), a speckle pattern on retina 44. This speckle pattern is at least partially back-reflected. In at least one further method step 68, the back-reflected speckle pattern exits pupil 64 again and is reflected again by the same refractive structures 14, 16 of HOE 18, so that it enters into laser projector 26. In at least one further method step 70, the back-reflected speckle pattern is detected by infrared detector 40. In at least one further method step 72, a beam path of the detected speckle pattern is analyzed and backtracked (mapped). With the aid of the analysis of the beam path of the speckle pattern back-reflected by eye 10, a visual defect of eye 10 is ascertained in method step 72. In at least one further method step 74, a development of a visual defect of eye 10 is ascertained with aid of an analysis of a temporal change of the beam path of the speckle pattern back-reflected by the same eye 10. For this purpose, results of visual defect analyses are regularly stored and are compared with one another for changes.

What is claimed is:

1. A method for a pupil detection and/or pupil tracking using an evaluation of a speckle pattern back-reflected by an eye of a light of an infrared laser irradiated into the eye, the method comprising:
   scanning at least the light of the infrared laser into the eye via a holographic optical element (HOE) that includes different refractive structures, the different refractive structures being configured in such a way that each generates a different visual defect correction; and
   evaluating the speckle pattern back-reflected by the eye of the light of the infrared laser scanned into the eye.

2. The method as recited in claim 1, wherein the different refractive structures are configured in such a way that respectively different focal points are generated in the eye for the light of the infrared laser irradiated into the eye.

3. The method as recited in claim 1, wherein a visual defect of the eye is ascertained using an analysis of a beam path of the speckle pattern back-reflected by the eye.

4. The method as recited in claim 1, wherein a development of a visual defect of the eye is ascertained using an analysis of a temporal change of a beam path of the speckle pattern back-reflected by the eye.

5. An optical system, comprising:
   a laser projector configured to at least generate a scanned infrared laser beam; and
   a holographic optical element (HOE) that includes different refractive structures;
   wherein the optical system is configured scan at least the laser beam of the infrared laser into an eye via the HOE, wherein the different refractive structures are configured in such a way that each generates a different visual defect correction.

6. The optical system as recited in claim 5, wherein the HOE has a segmented configuration, at least two different segments of the HOE including different refractive structures for different visual defect corrections.

7. The optical system as recited in claim 5, wherein the different refractive structures are situated in the HOE in a linear manner or in a regular pattern made up of rhombuses, or triangles or other shapes.

8. The optical system as recited in claim 7, wherein lines or pattern fields of the HOE that include the different refractive structures have a sufficiently large spatial extension which allows for a mapping of a back-reflected speckle pattern for ascertaining a respectively optimal refractive structure.

9. The optical system as recited in claim 7, wherein lines or pattern fields of the HOE that include the different refractive structures have a spatial extension which is smaller than that required for a mapping of a back-reflected speckle pattern.

10. The optical system as recited in claim 5, further comprising:
    an infrared detector configured to detect a reflection of the infrared laser beam back-reflected by a retina of the eye, opposite a laser emitting direction of the infrared laser beam.

11. Smart glasses configured for a pupil detection and/or pupil tracking using an evaluation of a speckle pattern back-reflected by an eye of a light of an infrared laser irradiated into the eye, the smart glasses configured to:
    scan at least the light of the infrared laser into the eye via a holographic optical element (HOE) that includes different refractive structures, the different refractive structures being configured in such a way that each generates a different visual defect correction; and
    evaluate the speckle pattern back-reflected by the eye of the light of the infrared laser scanned into the eye.

* * * * *